United States Patent [19]

Wong

[11] Patent Number: 5,163,332
[45] Date of Patent: Nov. 17, 1992

[54] GAS SAMPLE CHAMBER

[75] Inventor: Jacob Y. Wong, Santa Barbara, Calif.

[73] Assignee: Gaztech International Corporation, Goleta, Calif.

[21] Appl. No.: 793,990

[22] Filed: Nov. 18, 1991

Related U.S. Application Data

[63] Continuation-in-part of Ser. No. 604,615, Oct. 26, 1990, abandoned, which is a continuation-in-part of Ser. No. 503,216, Apr. 2, 1990, Pat. No. 5,060,508.

[51] Int. Cl.$^5$ ............................................. G01N 1/00
[52] U.S. Cl. ............................. 73/863.23; 73/31.02; 356/437
[58] Field of Search ........... 73/863.23, 863.81, 864.81, 73/31.01, 31.02, 31.05; 250/338.5, 343, 352, 344–346, 436; 356/437, 440; 340/632

[56] References Cited

U.S. PATENT DOCUMENTS

| | | | |
|---|---|---|---|
| 3,966,439 | 6/1976 | Vennos | 73/863.22 |
| 4,155,247 | 5/1979 | Kaczmarek et al. | 73/863.23 |
| 4,709,150 | 11/1987 | Burough et al. | 250/338.5 |
| 4,749,276 | 6/1988 | Bragg et al. | 250/343 |
| 4,800,272 | 1/1989 | Harley et al. | 250/255 |
| 4,947,578 | 8/1990 | Anderson et al. | D22/122 |

FOREIGN PATENT DOCUMENTS

| | | | |
|---|---|---|---|
| 0173734 | 10/1984 | Japan | 356/437 |
| 0105947 | 6/1985 | Japan | 356/437 |
| 0298031 | 12/1988 | Japan | 356/437 |

*Primary Examiner*—Robert Raevis
*Attorney, Agent, or Firm*—Daniel C. McKown

[57] ABSTRACT

A diffusion-type gas sample chamber for use in a gas analyzer consists of an elongated hollow tube having an inwardly-facing specularly-reflective surface that permits the tube to function also as a light pipe for transmitting radiation from a source to a detector through the sample gas. A number of filtering apertures in the wall of the otherwise non-porous hollow tube permit the sample gas to enter and exit freely under ambient pressure. Particles of smoke and dust of a size greater than 0.1 micron are kept out of the chamber by use of a semi-permeable membrane that spans the apertures in the hollow tube. Condensation of the sample gas components is prevented by heating the sample chamber electrically to a temperature above the dew point of the component of concern.

6 Claims, 1 Drawing Sheet

GAS SAMPLE CHAMBER

REFERENCE TO RELATED APPLICATIONS

This application is a continuation-in-part of U.S. application Ser. No. 07/604,615 filed Oct. 26, 1990, now abandoned, which was a continuation-in-part of U.S. application Ser. No. 07/503,216 filed Apr. 2, 1990 and issued Oct. 29, 1991 as U.S. Pat. No. 5,060,508 for "Gas Sample Chamber."

FIELD OF THE INVENTION

The present invention is in the field of gas analyzers and specifically relates to a diffusion-type sample chamber for use in a gas analyzer of the type known as an NDIR (nondispersive infrared) analyzer.

THE PRIOR ART

The NDIR technique has long been considered one of the best methods for gas measurement. In addition to being highly specific, the NDIR gas analyzers are also very sensitive, stable, reliable, and easy to maintain. The major drawback of the NDIR gas measurement technique has been its complicated and expensive implementation.

An NDIR gas analyzer typically includes an infrared source, a motor-driven mechanical chopper to modulate the source so that synchronous detection can be used, a pump to push or pull gas through a sample chamber, a bandpass filter, a sensitive infrared detector plus expensive infrared optics and windows to focus the infrared energy from the source onto the detector. Thus, despite the fact that the NDIR gas measurement technique is one of the best, it has not found wide application because of its complexity and high cost of implementation.

The present invention significantly simplifies the implementation of the NDIR gas measurement technique, and this simplification results in a concomitant reduction in cost, thereby opening dozens of applications for the NDIR technique that were heretofore considered impractical because of cost or complexity.

For example, the sample chamber of the present invention is at the heart of a much faster and sensitive carbon dioxide detector for use in sensing fires (U.S. Pat. No. 5,053,75 issued Oct. 1, 1991 to the present applicant), and is also at the heart of a ventilation controller or VENTOSTAT (the thermostat of ventilation as described in U.S. Pat. application Ser. No. 07/611,630 filed Jun. 6, 1991 for VENTILATION CONTROLLER by the present inventor), which is highly useful in combatting indoor air pollution by monitoring the concentration of carbon dioxide in the indoor air and bringing in fresh air when the carbon dioxide concentration is excessive.

The present invention for a simplified diffusion-type gas sample chamber provides a novel approach for reducing the complexity of NDIR gas measurement systems by eliminating the need for: expensive optics, mechanical choppers, and a pump for pulling or pushing the gas into the sample chamber. In addition, the sample chamber of the present invention provides a long effective pathlength which increases the detection sensitivity.

In U.S. Pat. No. 4,709,150 issued Nov. 24, 1987 to Burough et al., there is described a gas sample chamber that consists of a tube composed of a porous material such as plastic or a sintered metal. In contrast, the gas sample chamber of the present invention is composed of a gastight material; i.e., a nonporous material through which gas does not pass. Burough et al. teach that the pore size should be from 0.3 to 100 microns. There is no teaching or suggestion of using the walls of the porous tube as reflective radiation-guiding elements. Perhaps for this reason, the problem of condensation of the gas into droplets on the interior of the sample cell is not addressed.

Burough et al. do not teach or suggest multiple reflections from a specularly-reflective surface. This seriously affects the performance of their system. Without taking advantage of the radiation-collecting ability of the sample chamber, the system of Burough et al. has much poorer radiation collecting ability, leading to a lower signal-to-noise ratio. Furthermore, the system of Burough et al. does not have provision for a long pathlength, and hence the sensitivity of their system suffers in comparison with the present invention.

With regard to the diffusion of gas into the chamber of Burough et al., as compared to the present invention, it is noted that the porous material used in the sample chamber of Burough et al. is several hundreds of microns thick. In contrast, in the present invention, the diffusion into the sample chamber takes place through a semi-permeable membrane which is on the order of 25 to 50 microns thick. Accordingly, it takes much longer for the gas, or changes in the concentration in the gas, to diffuse into the chamber of Burough et al., as compared with the present invention. This greatly lengthens the response time of the chamber of Burough et al., thereby making it a poor choice for a fire detecting sensor, whereas the chamber of the present invention responds very rapidly to changes in the carbon dioxide concentration, and laboratory tests have demonstrated that the sample chamber of the present invention has an extremely fast response time, which is highly desirable in a fire detector.

In Japanese publication No. 59-173734(A), Miyazaki describes an infrared ray gas analysis meter in which radiation proceeds in parallel along a sample cell and a reference cell. These cells have the form of a helical tube.

Miyazaki's system, as disclosed in his patent, falls under the category of a conventional NDIR gas measurement system. Were it not for the fact that the incident radiation undergoes multiple reflections inside both the sample and reference cells, there would be no difference from a conventional NDIR system, and consequently no advantage at all. Miyazaki's design still calls for a mechanical chopper, pumps to direct gases through both the sample and reference cells, and two detectors. Thus, when these factors are taken into consideration, Miyazaki's invention does not come close in simplicity and efficiency to the present invention.

In U.S. Pat. No. 4,499,379 issued Feb. 12, 1985 to Miyatake et al. and in U.S. Pat. No. 4,501,968 issued Feb. 26, 1985 to Ebi et al., there is described a gas analyzer having a heated sample gas container for containing a sample gas at a temperature at which the component whose concentration is to be determined will emit infrared radiation of a characteristic wavelength. This gas analyzer works on an emission principle and is not a nondispersive infrared absorption analyzer. A heater in the wall of the sample cell heats the sample gas to temperatures of at least 100° C. to cause the gas to radiate infrared. This is said to increase the radiation relative to the radiation from the gas. The internal surface of the sample cell is said to be a mirror surface, but the patents give no reason for this. Since the gas itself is the source of the radiation, which is isotropic, it does not appear that the walls of the chamber would serve to guide the radiation in any useful way.

In U.S. Pat. No. 3,966,439 issued Jun. 29, 1976 to Vennos, there is described a fluid sampling device that includes a pump and that is used for accumulating a sample of particles found in the air, in factories, power plants, mines, etc.

Likewise, in U.S. Pat. No. 4,947,578 issued Aug. 14, 1990 to Anderson, et al. there is described a controlled release system for a volatile insect attractant. In this patent the attractant vapor is allowed to evaporate through a semipermeable membrane, the pore size being determined by the desired evaporation rate, and submicron pore sizes are recited.

SUMMARY OF THE INVENTION

It is the first objective of the diffusion-type gas sample chamber of the present invention to serve as a light pipe to efficiently conduct radiation from a source through a gas sample to a detector, while keeping particles of smoke and dust that are larger than 0.1 micron out of the sample chamber.

A second objective of the diffusion type gas sample chamber is to restrict access of unwanted contaminants, by size, so that they will not cause error in the measurement of the concentration of a particular gas, while at the same time permitting molecules of particular gas to freely enter and leave the sample chamber by diffusion only, through one or more filtering apertures.

In accordance with a preferred embodiment of the invention, the inwardly-facing surface of the sample chamber is specularly-reflective to serve as a light pipe to conduct radiation introduced at one end of the elongated sample chamber by a source to a detector located at the other end of the sample chamber.

Also in accordance with the present invention, one or more filtering apertures are included in the wall of the chamber, and these filtering apertures are each covered by a layer of a semi-permeable membrane that keeps particles larger than 0.1 micron from entering the space within the chamber.

It is a further objective of the invention to provide a diffusion-type gas sample chamber in which condensation of gases or vapors on the inwardly-facing walls of the sample chamber can be prevented.

In accordance with a preferred embodiment of the invention, means are provided for heating the sample chamber so that its temperature is above the dew point of any gas or vapor that might have a tendency to condense on the inwardly-facing specularly-reflective surface of the sample chamber.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
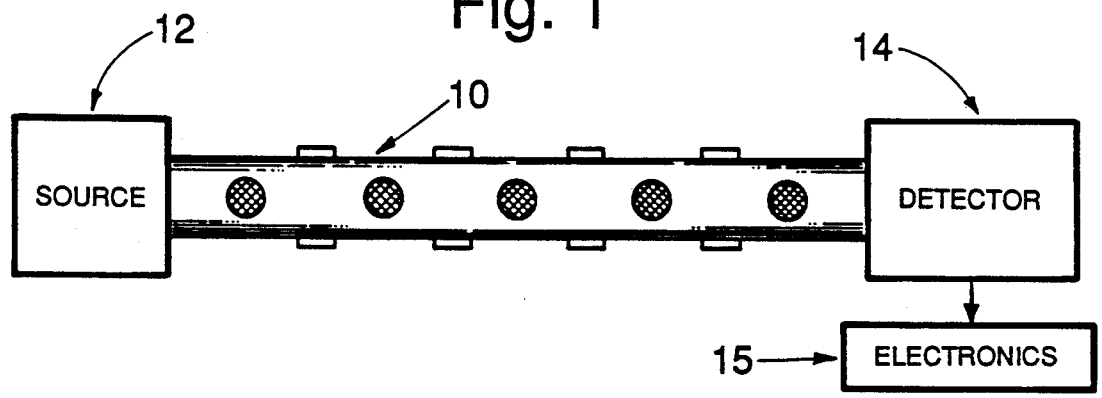
FIG. 1 is a side elevational view showing the major parts of a gas analyzer in accordance with the present invention.

As shown in FIG. 1, a gas analyzer includes a source chamber 12 that contains a source of radiation. The source may be a small incandescent lamp and the radiation may be visible light and/or infrared radiation produced by the lamp. The source chamber 12 is connected to a gas sample chamber 10 that includes a gas sample, present by diffusion only, to be analyzed to determine the concentration of a particular gaseous component. Radiation from the source chamber 12 passes through the gas sample that is contained in the gas sample chamber 10, and thereafter the radiation falls on a detector located in the detector chamber 14. The detector produces an electrical signal that represents the intensity of the radiation falling on it. To enhance the sensitivity of the device, it is well known to place a narrow pass band filter in the optical path in front of the detector, so that the detector receives mainly radiation of a wavelength that is strongly absorbed by the gas whose concentration is to be determined. The electrical signal produced by the detector is applied to an electronic circuit !5 that converts it to a signal that represents the concentration of the gas in question.

Figure 2:
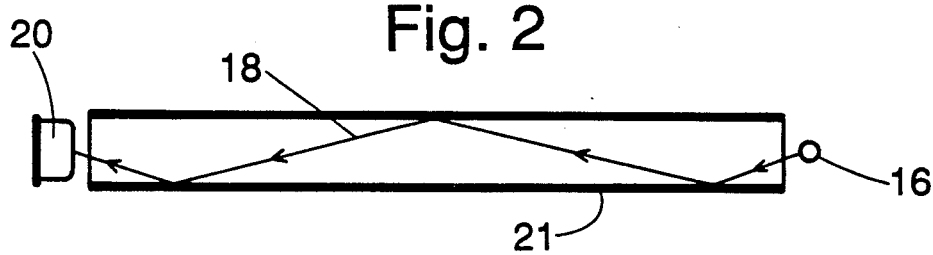
FIG. 2 is a simplified optical diagram showing the path of a typical ray of radiation through the gas sample chamber; and, FIG. 3 is a fractional cross-sectional view of a diffusion-type gas sample chamber in accordance with a preferred embodiment of the present invention.

FIG. 2 is a simplified optical diagram showing the optical path taken by a typical ray 18 emitted by the source 16 as the ray is multiply reflected while passing down the length of a tube portion 21 of the gas sample chamber 10, and eventually falls on the detector 20.

Figure 3:
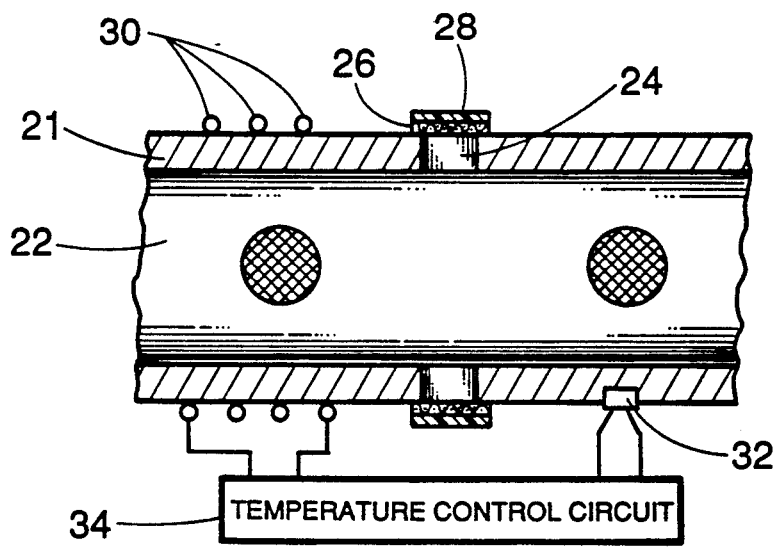

FIG. 3 is a fractional cross-sectional view through the gas sample chamber 10 shown in more detail. The body of the gas sample chamber is an elongated hollow tube 21 of nonporous (gastight) material having an inwardly-facing specularly-reflective surface 22. In the preferred embodiment, this surface 22 is a unitary portion of the inner surface of the tube 21 while, in an alternative embodiment, the surface may be an applied coating or a layer of a specularly-reflective material.

The elongated hollow tube 21 includes at least one filtering aperture, of which the filtering aperture 24 is typical. These filtering apertures are necessary to permit ambient gases to enter and leave the sample chamber by diffusion through the semipermeable membrane. However, it is not desirable that particles of dust and smoke should be able to enter the chamber freely, and, to that end, the filtering aperture 24 is covered by a sheet 28 of a semi-permeable membrane that keeps out particles of a size greater than 0.1 micron. To achieve high rates of diffusion for particles of size less than 0.1 micron, the sheet 28 of semi-permeable membrane must be quite thin, and therefore it is supported on a support means having the form of a mesh-like grid 26 that spans the filtering aperture 24. In the preferred embodiment, the semi-permeable membrane is composed of silicone rubber.

Because the gas sample chamber is always filled with gas, by virtue of free diffusion through the semipermeable membranes 28 that cover the filtering apertures (24), there is a possibility that if the ambient temperature falls sufficiently, water vapor or one of the other gases in the sample chamber will condense to a liquid state and be deposited in the form of small droplets on the specularly-reflective surface 22 as well as on the detector 20. This would interfere with the specular reflection that is needed for operation of the sample chamber, and would lead to erroneous results.

To prevent this from happening, and thus increase the efficiency and repeatability of the transmission of the radiation, in the preferred embodiment a heater wire 30 is deployed on the gas sample chamber 10. A thermistor 32 measures the temperature of the wall of the sample chamber. Both the thermistor and the heater wire are connected to a heater control circuit 34, which functions as a closed loop controller that operates in the well-known way to maintain the sample chamber at a set temperature.

Thus, there has been described a diffusion-type gas sample chamber in the form of an elongated tubular member having an inwardly-facing specularly-reflective surface that conducts radiation through the gas from a detector to a source. Dust and smoke particles are kept out of the sample chamber by a sheet of semipermeable membrane that spans one or more filtering apertures which extend through the wall of the sample chamber. The wall of the sample chamber may be heated to prevent condensation of gaseous components in the chamber, and in the preferred embodiment a preset temperature is maintained by a servo.

The foregoing detailed description is illustrative of a preferred embodiment of the invention, and it is to be understood that additional embodiments thereof will be obvious to those skilled in the art. The embodiments described herein together with those additional embodiments are considered to be within the scope of the invention.

I claim:

1. A diffusion-type gas sample chamber for transmitting radiation through gases present in the chamber only by ambient pressure diffusion through a plurality of filtering apertures formed in the chamber walls, comprising in combination:
    a) an elongated hollow tube composed of a gastight material and having a specularly-reflective surface on its inner walls for transmitting radiation introduced at one end of said tube to the other end of said tube by means of multiple reflections from said specularly-reflective surface;
    b) said tube including a plurality of filtering apertures arrayed along said tube for improving the diffusion into and out of the space within said tube; and,
    c) a sheet of a semipermeable membrane covering each of said plurality of filtering apertures, said semipermeable membrane permitting gases to diffuse through it under ambient pressure into and out of the space within said tube and preventing airborne particles larger than a predetermined size from entering said space.

2. The sample chamber of claim 1 further comprising support means spanning each of said plurality of apertures for supporting said sheet of a semipermeable membrane.

3. The sample chamber of claim 2 wherein said support means include mesh-like grids spanning said plurality of filtering apertures.

4. The sample chamber of claim 3 wherein said predetermined size is 0.1 micron.

5. The sample chamber of claim 4 further comprising means for heating said specularly-reflective surface to a temperature above the dew point of the gas in said space to prevent condensation on said specularly-reflective surface, thereby increasing the efficiency and repeatability of said transmitting.

6. The sample chamber of claim 5 wherein said means for heating includes a closed loop temperature controller comprising a temperature sensing element for inputting a temperature signal to a control circuit for controllably outputting a heating current to a current-to-heat converting means.

* * * * *